United States Patent [19]

Broecker et al.

[11] 4,436,833
[45] Mar. 13, 1984

[54] PREPARATION OF METHANOL SYNTHESIS CATALYST COMPRISING ZINC, COPPER AND ALUMINUM

[75] Inventors: Franz J. Broecker, Ludwigshafen; Karl-Heinz Gruendler, Limburgerhof; Laszlo Marosi, Ludwigshafen; Matthias Schwarzmann, Limburgerhof; Bruno Triebskorn; Guenter Zirker, both of Ludwigshafen, all of Fed. Rep. of Germany

[73] Assignee: BASF Aktiengesellschaft, Fed. Rep. of Germany

[21] Appl. No.: 478,995

[22] Filed: Mar. 25, 1983

Related U.S. Application Data

[60] Continuation of Ser. No. 253,662, Apr. 14, 1981, abandoned, which is a division of Ser. No. 82,526, Oct. 9, 1979, abandoned.

[51] Int. Cl.$^3$ .................. B01J 27/20; B01J 23/80; L01B 31/24; L07C 29/16
[52] U.S. Cl. ..................... 502/176; 423/419 P; 502/342; 518/713
[58] Field of Search .................. 252/463, 475, 443; 518/713; 423/419 P

[56] References Cited

U.S. PATENT DOCUMENTS

| | | | |
|---|---|---|---|
| 3,850,850 | 11/1974 | Collins | 252/465 |
| 3,920,717 | 11/1975 | Marion | 260/449.5 |
| 4,081,253 | 3/1978 | Marion | 260/449.5 |
| 4,111,847 | 9/1978 | Stiles | 260/449.5 |
| 4,126,581 | 11/1978 | Sugier et al. | 260/449.5 |

FOREIGN PATENT DOCUMENTS

| | | | |
|---|---|---|---|
| 1241429 | 6/1967 | Fed. Rep. of Germany | 252/475 |
| 399097 | 9/1973 | U.S.S.R. | 252/475 |

OTHER PUBLICATIONS

"Synthesis of Methanol From Carbon Monoxide & Hydrogen", Ind. & Eng. Chem.–by W. K. Lewis & Per K. Frolich, (Mar. 1928).

*Primary Examiner*—P. E. Konopka
*Attorney, Agent, or Firm*—Keil & Witherspoon

[57] ABSTRACT

A process for the preparation of methanol by reacting a gaseous mixture of carbon monoxide, carbon dioxide and hydrogen at an elevated temperature and under superatmospheric pressure over a catalyst which contains zinc, copper and aluminum, the catalyst being prepared from a co-crystalline material of the formula $Cu_{2.2}Zn_{2.8}(OH)_6(CO_3)_2$, containing aluminum hydroxide as a structual promoter, by calcination and reduction at from 160° to 350° C. The novel catalyst has the advantage of giving a substantially increased space-time yield and having a longer life.

8 Claims, 2 Drawing Figures

PREPARATION OF METHANOL SYNTHESIS CATALYST COMPRISING ZINC, COPPER AND ALUMINUM

This is a continuation of application Ser. No. 253,662, filed Apr. 14, 1981, now abandoned which is a division of Ser. No. 82,526, filed Oct. 9, 1979, now abandoned.

The present invention relates to a process for the preparation of methanol by reacting hydrogen, carbon monoxide and carbon dioxide and/or steam and/or oxygen over a catalyst which contains zinc, copper and aluminum, and to a process for the preparation of this catalyst.

The reaction of a mixture of carbon monoxide and hydrogen, with or without addition of carbon dioxide, over a catalyst under a pressure of from 30 to 400 atmospheres and at from 200° to 400° C., to give methanol, has been disclosed. The catalysts used are mostly zinc oxide/chromium oxide catalysts or copper oxide catalysts, which may contain additional oxides. The conventional processes are not yet fully satisfactory, for industrial operation, in respect of economy, yield of end product, simplicity of operation, space-time yield, activity and life of the catalyst.

German Patent Application P 20 56 612.5-42 published May 31, 1972, relates to a process for the preparation of methanol by reacting a gas mixture containing carbon monoxide, carbon dioxide and hydrogen, at an elevated temperature and under superatmospheric pressure, over a catalyst containing zinc, copper and aluminum, wherein the reaction is carried out at from 200° to 350° C. and under a pressure of from 50 to 250 atmospheres over a catalyst which has been obtained by precipitating a compound of the co-crystalline series $(Cu_xZn_y)Al_2(OH)_{16}CO_3 \cdot 4H_2O$ with an alkali metal carbonate or alkali metal bicarbonate or a mixture of these from aqueous solutions containing copper, zinc and aluminum salts, x and y being able to assume values of from 0.5 to 5.5 and the sum of x and y being 6.

The present invention relates to an improved process for the manufacture of methanol, wherein a catalyst is prepared from a co-crystalline material of the formula

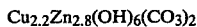

$Cu_{2.2}Zn_{2.8}(OH)_6(CO_3)_2$ which contains aluminum hydroxide as a structural promoter, by calcination and reduction at from 160° to 350° C.

It further relates to a process for the preparation of a catalyst, wherein the co-crystalline material is prepared by co-precipitation of the nitrates by means of sodium bicarbonate.

Figure 1:
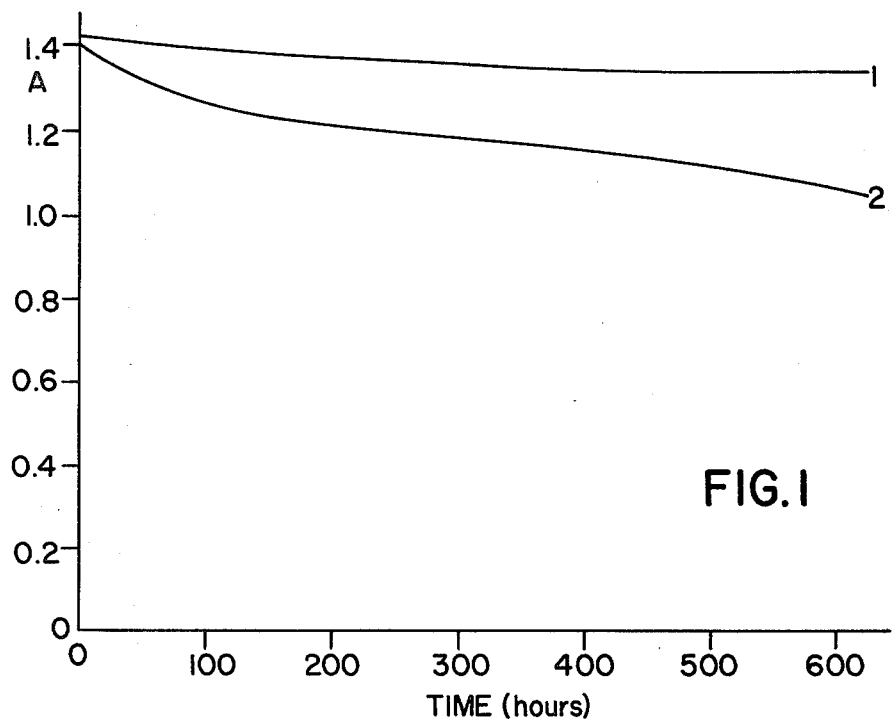
FIG. 1 shows the space-time yield of a catalyst according to the invention (curve 1), and a compartive catalyst (curve 2), as a function of process time (in hours)

The starting material used is advantageously a synthesis gas which has been prepared by partial oxidation of hydrocarbons and which, after being subjected to a combined $CO_2$ and $H_2S$ scrubbing, only contains CO and $H_2$, to which mixture from 1 to 5% by volume of steam are added.

According to this process, methanol is obtained by reacting hydrogen, carbon monoxide and carbon dioxide and/or steam and/or oxygen at from 200° to 350° C. and under a pressure of from 30 to 250 atmospheres over a catalyst which contains zinc, copper and aluminum in the following atom percentages: 38.5% of copper, 48.8% of zinc and 12.9% of aluminum. To prepare this catalyst, the components are converted into an easily decomposable co-crystalline material by co-precipitation with a carbonate or bicarbonate, eg. $NaHCO_3$, ie. in the lattice of the zinc hydroxide carbonate the zinc atoms are in part replaced at random by copper atoms, so that the components are very finely dispersed in one another even at the precipitation stage. The aluminum is co-precipitated as hydroxide and is very well dispersed in the co-crystalline matrix. Reduction, with simultaneous decomposition, of such co-crystalline material then gives copper finely dispersed in a matrix of fine zinc oxide crystals, with aluminum built into the matrix. Accordingly, the zinc oxide is aluminum-modified and gives, surprisingly, the increase in activity exhibited by the catalyst according to the invention. As a result of the fine dispersion of the copper in the matrix of fine zinc oxide crystals, recrystallization of the copper is minimal if the catalyst has the composition prescribed by the invention.

Compared to conventional processes, the process according to the invention gives methanol in substantially better space-time yield. Because of the lesser recrystallization, the life of the catalyst is increased, and because of the low copper content the cost of manufacture of the catalust is greatly reduced.

As the catalyst according to the invention has a higher activity, less catalyst need be used, and the reactor space can accordingly be made smaller. These factors improve the economics of the process, particularly in the case of sizable installations and continuous operation.

In addition to the steam reforming process for the production of synthesis gas, in which process the starting material, namely naphtha or natural gas, is first desulfurized, since the gas is produced over a nickel catalyst, there is a method of producing synthesis gas by partial oxidation of crude oils. In this process, for example, heavy fuel oil is combusted with oxygen and steam in a burner. Because of the high temperature of 1,400° C., the gas mixture produced has about the following composition: 47% by volume of CO, 48% by volume of $H_2$ and 5% by volume of $CO_2$.

The desired CO content can be obtained by partial conversion. The $H_2S$, COS and $CO_2$ can then be washed out (to residual contents of less than 1 ppm) by means of suitable scrubbing, and a synthesis gas containing CO and $H_2$ is then obtained, which, with addition of about 2% by volume of steam and/or from about 0.05 to 2% by volume of oxygen, can be used directly, by the process according to the invention, for the synthesis of methanol.

The starting material used for the process is advantageously a mixture of carbon monoxide, hydrogen and carbon dioxide and/or steam and/or oxygen, in which as a rule the gases are present in a ratio of from 0.06 to 0.25, preferably from 0.1 to 0.2, mole of carbon monoxide, from 0.01 to 0.2, preferably from 0.03 to 0.15, mole of carbon dioxide, from 0.01 to 0.07, preferably from 0.02 to 0.04, mole of steam and from 0.001 to 0.03 mole of oxygen per mole of hydrogen.

The starting materials can also contain gases which are inert under the reaction conditions, for example nitrogen, argon and methane, up to a total of about 5% by volume. The sulfur content and chlorine content of the mixture should advantageously be less than 0.1 ppm. The catalyst intermediate used is a co-crystalline material of the zinc hydroxide carbonate type, of the formula:

$$Cu_{2.2}Zn_{2.8}(OH)_6(CO_3)_2.$$

This aluminum-modified intermediate is either reduced directly, with simultaneous decomposition, or is first calcined at from 200° to 300° C. and then reduced.

In general, the catalyst used according to the invention is prepared as follows. A solution which contains the components, in the above weight ratio, in the form of their salts is added, at 90° C., to an aqueous solution of sodium bicarbonate. The metal salts are preferably nitrates, but other water-soluble salts, for example acetates, may also be used. During the precipitation, the solution is mixed thoroughly to prevent major concentration differences arising. X-ray methods can be used for rapidly testing whether the co-crystalline precipitate formed is satisfactory. The X-ray diffraction diagram of the co-crystalline material is characterized by at least the following d-values of the diffraction lines: 6.75; 3.70, 3.21; 2.90; 2.74; 2.64; 2.15; 1.94; 1.61.

The precipitate is filtered off and the filter residue is repeatedly washed with water until there is no further nitrate detectable in the filtrate. The filter residue is then dried at 110° C., after which it may or may not be calcined at from 250° to 300° C. The pulverulent material is then advantageously converted to coarse granules, for example by producing catalyst tablets of size 3×3 mm, or even larger, on a tableting machine. Granule sizes of from 3 to 8 millimeters are preferred. The tableting assistant used is preferably graphite, added in an amount of from 1 to 3 percent by weight, based on the calcined material. The press is advantageously operated at a pressure such that the bulk density of the tablets is from 1.0 to 1.5 kilograms per liter. As a rule, the tablets obtained are reduced with hydrogen, for example using a mixture of hydrogen and nitrogen containing from 0.5 to 30% by volume of the former, under atmospheric pressure, at a temperature raised stepwise from 160° to 230° C. After completion of the reduction, copper is essentially present as metal, and the other metals as oxides.

A reator suitable for high-pressure reactions, for example a tubular reactor or one of the multiple-bed type, is filled with the catalyst prepared according to the invention and the mixture of starting materials is passed through the reactor at the reaction temperature and reaction pressure. The throughput is preferably from 5 to 25, more especially from 10 to 20, cubic meters (S.T.P.) of starting mixture per liter of catalyst per hour. If desired, the reduction of the catalyst can be carried out in the reactor, followed by the reaction of the synthesis gas. The methanol is isolated from the reaction mixture, leaving the reactor, by conventional methods, for example by condensation.

EXAMPLE 1

(A) Preparation of the catalyst

To precipitate the catalyst components, two solutions are prepared:

Solution 1: 1.33 kg of copper nitrate, 2.1 kg of zinc nitrate and 0.278 kg of aluminum nitrate are dissolved in 15 liters of water.

Solution 2: 2.344 kg of sodium bicarbonate are dissolved in 15 liters of water.

The two solutions are separately heated to 90° C. and solution 1 is then added rapidly, in the course of from 1 to 2 minutes, to solution 2, whilst stirring. The mixture is stirred for a further 15 minutes and the precipitate is then filtered off and washed nitrate-free with water. The filter cake is dried at 110° C. and then calcined for 4 hours at 270° C. under a nitrogen atmosphere. The calcined product is comminuted to a particle size of less than 1 mm and after having been mixed with 2 percent by weight of graphite is molded into 3 mm pills. The bulk density of the catalyst thus prepared is 1.138 g/cm$^3$.

(B) Preparation of methanol 300 cm$^3$ of the above catalyst are fitted into a tubular reactor and are reduced at atmospheric pressure with a mixture of 1% by volume of $H_2$ and 99% by volume of $N_2$. The reduction is carried out successively for 8 hours at 150° C., 8 hours at 170° C. and 8 hours at 190° C., after which the temperature is raised to 230° C.

At 230° C., the synthesis gas consisting of 72.6% of $H_2$, 21.5% of CO, 5.1% of $CO_2$ and 0.8% of inert gases is passed into the reactor. The following experimental conditions are selected for quasi-adiabatic operation:

| | |
|---|---|
| Entry temperature | 230° C. |
| Pressure | 50 atmospheres |
| Throughput | 10,000 liters (S.T.P.)/liter of catalyst.h |

This gives a space-time yield of 1.43 kg of methanol/liter of catalyst.h. The condensed crude product contains 96% of methanol and 3.4% of water in addition to small amounts of inorganic impurities. FIG. 1 shows the space-time yield of this catalyst as a function of the duration of operation.

Curve 1: metal content of the catalyst in atom %: Cu 38.3; Zn 48.8; Al 12.9.

By way of comparison, the Figure also shows the results for a catalyst which contains a larger amount of copper than the catalyst according to the invention.

Curve 2: metal content of the (comparative) catalyst in atom %: Cu 61.6; Zn 28.1; Al 10.9.

The great decrease in the space-time yield by increased recrystallization of the copper, particularly at the start of the experiment, can be seen from the graph.

(C) Effect of steam

The catalyst, prepared as described above, was fitted into a tubular reactor and the latter was fed with a synthesis gas of the following composition: 74.8% by volume of $H_2$, 21.8% by volume of CO, 2.7% by volume of $H_2O$ and 0.7% by volume of inert gases. The space-time yield is 1.42 kg of methanol per liter of catalyst per hour.

This experiment shows that the catalyst used according to the invention is particularly stable to steam.

EXAMPLE 2

Figure 2:
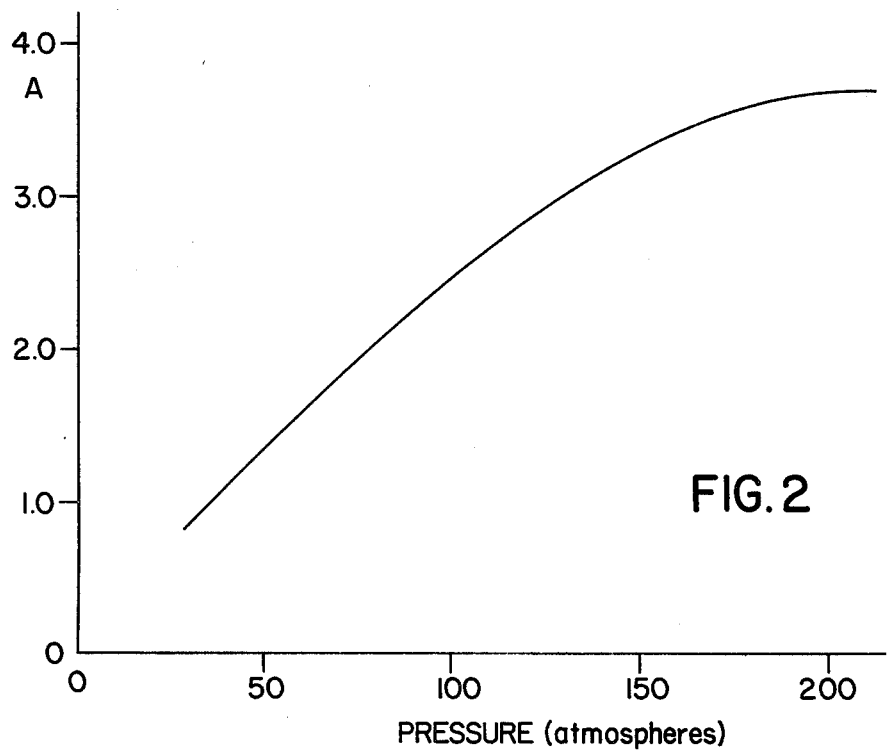
FIG. 2 shows the space-time yield of another catalyst according to the invention as a function of the pressure.

A catalyst is prepared by co-precipitation of the nitrates of the components and after drying, calcining and molding has the following composition in percent by weight: 34.1% of zinc, 27.5% of copper and 3.3% of aluminum. This catalyst is fitted into a tubular reactor and the latter is fed with a synthesis gas consisting of 75.4% of $H_2$, 20% of CO, 4.2% of $CO_2$ and 0.4% of inert gases. The space-time yield is determined as a function of the pressure. The results are shown in FIG. 2.

We claim:

1. A process for the preparation of a catalyst, for methanol synthesis, from a mixed crystalline material of the formula $$Cu_{2.2}Zn_{2.8}(OH)_6(CO_3)_2$$

which contains aluminum hydroxide as a structural promoter, wherein the improvement comprises co-precipitating copper, zinc and aluminum nitrates or acetates with sodium bicarbonate.

2. The process of claim 1, wherein the zinc, copper and aluminum are nitrates.

3. The process of claim 1, wherein said catalyst is comminuted.

4. The process of claim 2 wherein said catalyst is comminuted.

5. The process of claim 1, wherein said mixed crystalline material of the formula $$Cu_{2.2}Zn_{2.8}(OH)_6(CO_3)_2$$

has an X-ray diffraction diagram characterized by at least the following d values of the diffraction lines: 6.75; 3.70; 3.21; 2.90; 2.75; 2.64; 2.15; 1.94; and 1.61.

6. The process of claim 5, wherein the zinc, copper and aluminum are nitrates.

7. The process of claim 5, wherein said catalyst is comminuted.

8. The process of claim 6, wherein said catalyst is comminuted.

* * * * *

UNITED STATES PATENT AND TRADEMARK OFFICE
CERTIFICATE OF CORRECTION

PATENT NO. : 4,436,833
DATED : March 13, 1984
INVENTOR(S) : Franz Josef BROECKER et al.

It is certified that error appears in the above-identified patent and that said Letters Patent is hereby corrected as shown below:

ON THE COVERING PAGE:

Please add:

[30] FOREIGN APPLICATION PRIORITY DATA

October 26, 1978 [DE] Fed. Rep. of Germany...2846614

Signed and Sealed this

Twenty-fifth Day of December 1984

[SEAL]

Attest:

Attesting Officer

GERALD J. MOSSINGHOFF

*Commissioner of Patents and Trademarks*